(12) United States Patent
Hök et al.

(10) Patent No.: US 7,919,754 B2
(45) Date of Patent: Apr. 5, 2011

(54) BREATH ANALYZER

(75) Inventors: Bertil Hök, Västerås (SE); Håkan Pettersson, Floda (SE)

(73) Assignee: Autoliv Development AB, Vargarda (SE)

( * ) Notice: Subject to any disclaimer, the term of this patent is extended or adjusted under 35 U.S.C. 154(b) by 285 days.

(21) Appl. No.: 11/657,817

(22) Filed: Jan. 25, 2007

(65) Prior Publication Data

US 2008/0061238 A1    Mar. 13, 2008

(51) Int. Cl.
*G01J 5/02* (2006.01)

(52) U.S. Cl. ........... 250/339.13; 250/338.1; 250/339.01; 250/339.06; 250/339.12

(58) Field of Classification Search ............. 250/339.01, 250/339.06, 339.12, 339.13, 343
See application file for complete search history.

(56) References Cited

U.S. PATENT DOCUMENTS

| | | | |
|---|---|---|---|
| 3,505,022 A | | 4/1970 | Luckey |
| 3,792,272 A | * | 2/1974 | Harte et al. ............ 250/343 |
| 5,282,473 A | * | 2/1994 | Braig et al. ............ 600/532 |
| 5,376,555 A | | 12/1994 | Forrester et al. |
| 5,401,966 A | * | 3/1995 | Gray et al. ............ 250/343 |
| 5,418,366 A | * | 5/1995 | Rubin et al. ............ 250/338.5 |
| 5,515,859 A | * | 5/1996 | Paz ............ 250/339.13 |
| 5,971,937 A | | 10/1999 | Ekstrom |
| 6,844,554 B2 | * | 1/2005 | Karlsson ............ 250/339.13 |
| 2003/0109795 A1 | * | 6/2003 | Webber ............ 600/543 |
| 2003/0136600 A1 | | 7/2003 | Breed |
| 2004/0129056 A1 | * | 7/2004 | Hok et al. ............ 73/24.06 |
| 2006/0044144 A1 | * | 3/2006 | Duval ............ 340/576 |
| 2010/0025585 A1 | * | 2/2010 | Taguchi et al. ............ 250/339.13 |

FOREIGN PATENT DOCUMENTS

| | | |
|---|---|---|
| DE | 42 35 328 A1 | 4/1994 |
| EP | 0 752 584 A2 | 1/1997 |
| EP | 1 441 212 A1 | 7/2004 |

* cited by examiner

*Primary Examiner* — David P Porta
*Assistant Examiner* — Casey Bryant
(74) *Attorney, Agent, or Firm* — Brinks Hofer Gilson & Lione

(57) ABSTRACT

A system for the detection and analysis of at least one volatile substance in breath samples of a subject, including at least one source of infrared radiation adapted to the wavelength range of specific absorption peaks of said substances, a plurality of reflecting surfaces of said radiation adapted for collimation onto at least one detector providing a plurality of electrical output signals corresponding to the transmission of said radiation within wavelength intervals corresponding to said absorption peaks, at least one measuring cell including a mechanical support structure defining the position of said source, reflecting surfaces and detector, adapted to the reception and disposal of said breath sample, and exposing it to said radiation, at least one electronic signal processing unit with capacity to analyse said signals with respect to pre-programmed information concerning infrared absorption spectra of said substances. The response of the system being displayed or otherwise communicated, and perceived as essentially instantaneous.

48 Claims, 3 Drawing Sheets

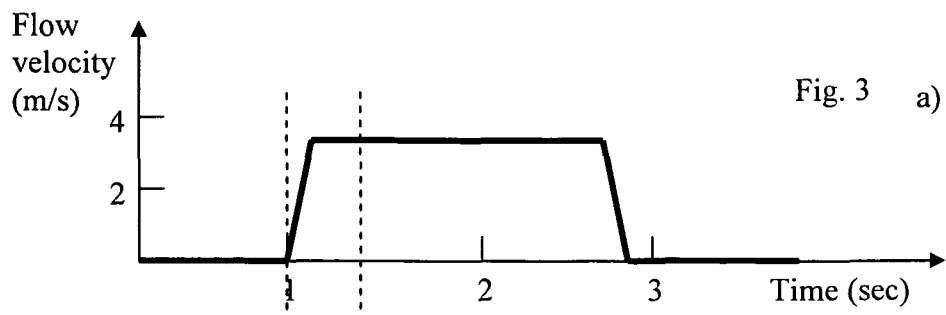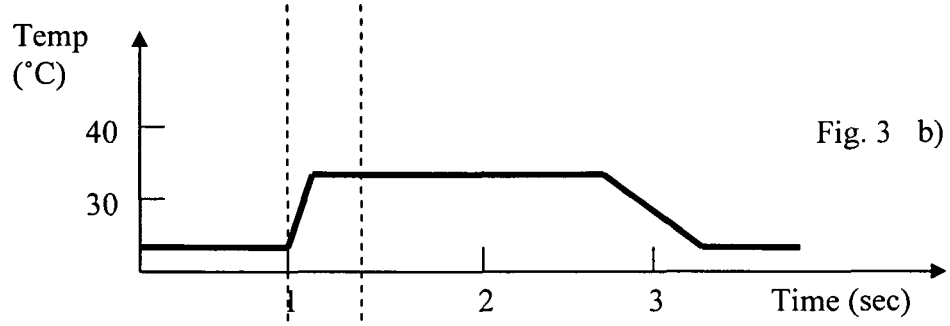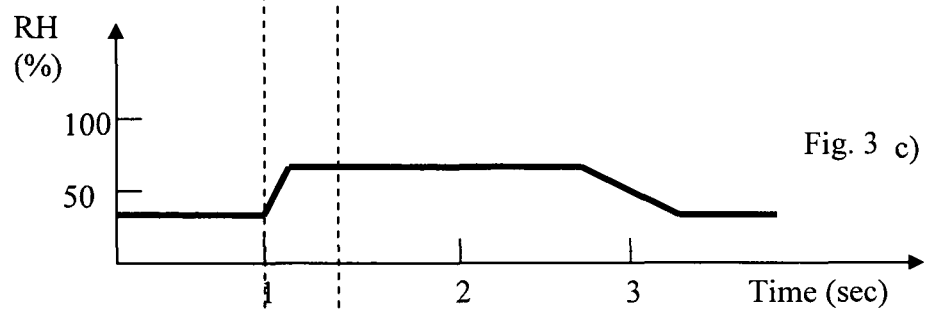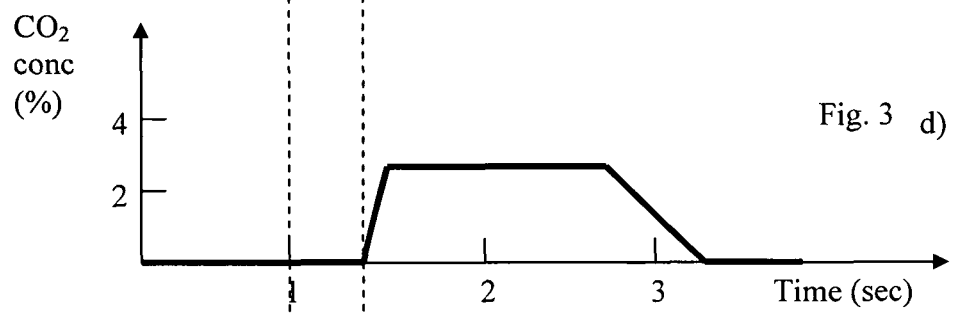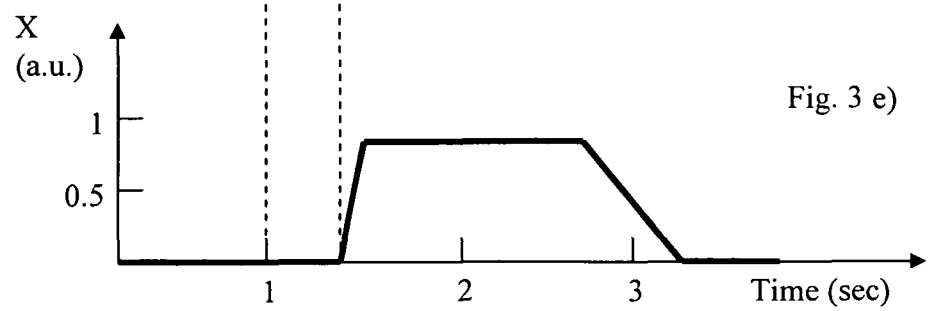

BREATH ANALYZER

CROSS REFERENCE TO RELATED APPLICATION

This application claims priority to GB 06 8051.7 filed Sep. 13, 2006 which is currently pending.

FIELD OF THE INVENTION

The present invention is concerned with the detection and analysis of substances within breath samples from subjects. One field of application of significant importance is the determination of alcohol concentration in vehicle drivers, but the field encompasses the detection of any volatile substance for any reason in breath samples. Technologically, it is preferred to use the present invention with those volatile substances exhibiting distinctive absorption properties of infrared radiation, thus allowing their identification and quantification.

BACKGROUND

It is generally known that the constitution of undiluted samples of air expired from the lungs of a subject is tightly linked to the corresponding blood constitution. This is due to the extremely large surface area of normal lung tissue, including the alveoli combined with a network of fine capillary blood vessels, resulting in efficient gas exchange. Measurement of end tidal gas concentrations, i e the value obtained at the end of the respiratory cycle, is thus replacing arterial blood sampling in clinical physiology. Furthermore, breath sampling is now being accepted in many countries as an evidential method for the assessment of blood alcohol concentration in vehicle drivers.

The reliability, speed and ease with which breath sampling can be accomplished is, of course, a central issue. For example, in the case of alcohol interlocks for vehicle drivers, the risk of false output from the analysis should be brought down to an absolute minimum. A large sample volume is normally required in order to obtain high resolution, opposite to the requirement of fast response, which favours a small sample volume. Only a very small fraction of samples will actually result in the positive detection of alcohol, and sober drivers will not accept a cumbersome, and time-consuming testing procedure. A further complication is that such a device should operate with maintained accuracy also at extreme environmental conditions.

Breath sampling is commonly performed with a mouthpiece to ensure that the sample is undiluted. Typically, the mouthpiece consists of a piece of polymer tubing with openings to expose the sensor to the breath sample. Mouthpieces are disposable items for hygienic reasons, and their handling and cost are major limitations to the widespread use of breath analysing equipment in e g alcohol interlock systems.

Recently, it was demonstrated that the simultaneous measurement of carbon dioxide and another substance of interest in the vicinity of a subject may provide a novel possibility of quantitative assessment of the blood concentration of that substance. It has been demonstrated that the ratio of the two externally measured concentrations multiplied by the alveolar concentration of carbon dioxide will provide an approximation of the actual blood concentration of the substance. The variability of alveolar $CO_2$ concentration is limited and predictable to a large extent, and may therefore be estimated with fair accuracy. The new technique may eliminate the need for a mouthpiece, except when very high measurement accuracy is required.

It is further generally known that many substances in the gas phase exhibit distinctive absorption spectra in the infrared wavelength range between approximately 1 and 10 μm. In fact, absorption spectroscopy is a major tool to determine the composition of unknown gas samples. This is due to quantum mechanical transitions between energy levels of molecular vibrations. Carbon dioxide, for example, exhibits a strong absorption peak at a wavelength of approximately 4.26 μm, corresponding to an asymmetric stretch mode of vibration, in which the central carbon atom vibrates in opposition to the two oxygen atoms along the linear axis of the molecule. Ethyl alcohol exhibits distinctive absorption peaks at 3.4 and 9.4 μm, also corresponding to molecular vibratory states. Water vapour, for comparison, exhibits absorption peaks at 2.8 and 6.2 μm. Determination of water vapour corresponds to the measurement of absolute humidity. Relative humidity may be calculated from this if temperature is known. The simultaneous measurement of humidity in breath samples may be of interest, as will be further described below.

Infrared absorption spectroscopy may involve measurement of the transmission of infrared radiation through the sample from a source of radiation and a detector. Typically, a dispersive element is also introduced in the radiation path, whereby radiation at certain wavelength intervals only, are transmitted to the detector. A diffraction grating or an interference filter could serve as a dispersive element. By varying the angle of incidence, it is possible to vary the accepted wavelength interval. In a scanning spectrometer, the wavelength interval is successively scanned, allowing a certain range of wavelength intervals to be analysed, and thereby the detection of multiple absorption peaks corresponding to one or several substances.

When certain substances are being monitored alone, it is customary to use interference filters as dispersive elements, with transmission properties matched to the absorption peaks of those substances. State-of-the-art interference filters with excellent properties can be produced at low cost, and can be integrated with infrared detectors, e g of the thermopile type.

In photoacoustic spectroscopy, a pulsed radiation source with filter matching certain absorption peaks is being used. In the presence of an absorbing substance, heat pulses synchronous with the radiation pulsations may be detected by a sensitive microphone. This solution is attractive for the detection of substances with very low concentration due to favourable noise characteristics. On the other hand, it is more complex and expensive, especially when a plurality of substances are involved.

Transmission measurements are advantageous from the point of view of reliability. A transmission spectrometer may include self-monitoring functions, including all vulnerable elements. It may, for example, monitor the output from the infrared source, enabling compensation for eventual long term drift.

A technological challenge not solved in state-of-the-art infrared spectrometers is to combine high measurement resolution with fast response. Ideally, the system should respond and recover as fast as normal human perception, i e within a few seconds. On the other hand, the demands on high resolution of weakly absorbing substances infer relatively long radiation transmission paths, of the order of several tens of centimeters. As already pointed out, these requirements are in opposition.

Further difficulties are related to the legal aspects related to the collection and analysis of breath samples from human subjects. The demands on reliability and traceability of eventual errors are exceptionally high. Possible attempts to manipulate the analysing process should be detected in order to allow adequate measures.

A difficulty specifically related to the analysis of breath samples, and the simultaneous $CO_2$ measurement, is the fact that the $CO_2$ concentration in breath samples is typically in the percent range, whereas the concentration of other substances is typically several orders of magnitude lower. It is thus necessary to minimise cross sensitivities, i e the interdependencies between the various determinations, and the large difference in concentrations is a complication.

It may be of interest to perform breath sampling outdoors, and at extreme environmental conditions. State-of-the-art infrared spectrometers are mainly used in laboratory-like environments. It is therefore an objective of the present invention to minimise the environmental influences, and to improve the durability to extreme conditions.

A further objective of the present invention is that the system should allow implementation at high production volumes, and at very low fabrication cost. Physically, it should be useable as a handheld stand-alone unit, or as an embedded system, e g in a vehicle.

GENERAL DESCRIPTION OF THE INVENTION

The present invention is directly addressing the problems indicated above, and specifically directed towards the analysis of breath samples collected in free air in the close vicinity of a subject. The method and system according to the invention is, however, likewise applicable for the analysis of an undiluted breath sample, using a mouthpiece for collection.

The breath analyser according to the invention includes:
at least one source of infrared radiation adapted to the wavelength range of absorption peaks of the substances to be analysed
reflecting surfaces
element for wavelength dispersion
detector providing output signals corresponding to the transmission within specified wavelength intervals
electronic signal processing unit with capacity to signal analysis with respect to pre-programmed information concerning infrared absorption spectra
support structure adapted to the immediate radiation exposure of the breath sample.

The support structure defines a measuring cell in which the infrared radiation is transmitted, and which allows the breath sample to be collected and disposed of, with minimum transit time. This transit time will determine the system response and recovery time. The former is defined by the process of detection and analysis, whereas the recovery is associated with the washout of the breath sample from the measuring cell. Only after completion of both these processes, will the system be ready to receive another breath sample. Typically, readiness is related to stable input signals, and may be communicated to the user or subject with instructions to deliver a breath sample.

The measuring cell is adapted for positioning within the expiratory airflow in close vicinity of the subject. The response of the system according to the invention to the detection and analysis of substances is perceived as essentially instantaneous, i e within a few seconds. The measuring cell typically has a tubular structure, with inlet and outlet openings large enough not to impede transit gas flow. Eventual regions of stagnant flow should not occupy more than 10% of the radiation transmission path. The system may also include means for the active transport of breath sample from the close subject vicinity to the support structure.

The transit time for the breath sample to pass through the measuring cell will determine the system response and recovery time $\tau_{rr}$. An approximate relation for its calculation is given by $$\tau_{rr} = \frac{L}{K \cdot v} \qquad (1)$$

L is the physical length of the measuring cell, v is the air flow velocity of the breath sample, and K is the ratio between the internal and external flow velocities. In the ideal case of a thin-walled tubular structure, K would be close to 1. Realistically K=0.1-0.2 in a typical system design. Inserting L=100 mm and v=1 m/sec results in $\tau_{rr}$=0.5-1 sec. The requirement of matching the system response and recovery time to the visual reaction time of typical subjects could thus be considered realistic.

Another factor that may influence the response time is the periodicity of modulation of the radiation source. However, even in the case of a heated filament, a modulation period considerably shorter than the visual reaction time of normal subjects can be used.

The relation between input and output radiation intensity, $I_i$ and $I_o$ of the measuring cell is given by:

$$I_o = I_i \cdot \exp(-C \cdot \alpha_\lambda \cdot l) \qquad (2)$$

where l is the length of the radiation path, C the concentration and $\alpha_\lambda$ the absorption coefficient of the substance at wavelength $\lambda$. By measuring $I_i$ and $I_o$ and using known values of $\alpha_\lambda$ and l, it is thus possible to determine the concentration C of a substance. The reliability of such a determination can be considerably improved by the parallel determination of several substances, some of which may be completely or partly known, both with respect to identity and concentration. Breath samples always include water vapour and carbon dioxide which may thus serve as reference substances.

The radiation path length l is preferably considerably larger than the physical dimensions of the measuring cell. This is accomplished by means of an arrangement of reflecting surfaces, or mirrors. Preferably, the reflecting surfaces are at least partly concave, exhibiting a reflectance coefficient (defined as the ratio between the reflected and incident intensities) exceeding 0.95. Consequently, the radiation will at least partly be collimated.

The dispersive element may either be a diffractive grating, or an interference filter, or a combination of these. It may also incorporate a substrate material having distinctive absorption properties, e g for suppressing high-order diffraction or interference. Using MEMS technology (micro electro-mechanical systems) the radiation scattering properties of a high-resolution diffraction grating may be controlled electronically. Using such a device, the exact spectral properties may be accurately controlled, also allowing switching between various modes.

Typically, a number of detector elements are being used, preferably thermopile or pyroelectric elements. The resolution of an optimised system according to the invention is limited by fundamental thermal noise within the detector, rather than environmental interference.

Further, the electronic signal processing unit includes a memory device for temporary and permanent information storage, and a device for the execution of pre-programmed sequence of logical and arithmetic operations, such as the execution of the algorithm (2) for several substances. These operations will typically be executed sequentially using conventional computer architectures, but will not add significantly to the system response time.

In the method according to the invention, the point of breath sampling may be located in the near vicinity of the subject's mouth/nose region, but not necessarily in physical contact with it. Preferably, it involves the proper positioning of the multivariable measuring cell, allowing expired air to flow through and past it. This may or may not require the active cooperation of the subject. The breath sample may be somewhat diluted with ambient air when it arrives at the point of measurement. Specific characteristics of expired air, such as time variation profiles of flow velocity, temperature, humidity, and carbon dioxide concentration are being analysed, providing categorisation of a certain event as approved or disapproved sample.

The breath sampling may involve instruction of the subject to expire against a specified sensing area. In a cooperative subject, this will result in a forced expiration of 0.5-1.5 liters of expired air which may be sampled at a distance of 20-50 cm. Passive sampling from a non-cooperative subject is also possible but requires closer proximity, typically 10-20 cm, due to the smaller flow velocities and volumes associated with relaxed expiration.

The described sampling procedure eliminates the need for a mouthpiece, which is otherwise mandatory in breath sampling equipment. The use of a diluted sample assumes an adequate estimation of the alveolar carbon dioxide concentration. When high accuracy is required, the described procedure may be followed by one employing a mouthpiece, and thereby eliminating the variations due to the estimation.

The unknown substances to be determined could be ethyl alcohol, or any other agent affecting the subject's health or behaviour. As already mentioned, measurement of carbon dioxide and water vapour concentration is preferably included as reference. The system may also include another reference detector operating at an infrared wavelength interval without known substance absorption. The inclusion of such a detector may e g serve the purpose of detecting temporary or permanent signal loss due to deposition onto the reflecting surfaces of condensed water droplets or dust particles. A suitable wavelength interval for such a reference detector would be 3.9 μm, which is unaffected by most substances of interest.

The system according to the invention also includes indicator or display means, or other means of signal communication. This may partly be directed towards the subject for providing a breath sample by forced expiration to the measuring cell.

Preferably, the support structure is transformable between one active operational condition in which at least one opening to receive a breath sample is provided, and one passive condition, in which the source, reflecting surface, dispersive element, and detector are protected from ambient exposure. This transformation is preferably provided by electromechanical means, whereby alternation between the conditions is partly or fully automatic.

The system according to the invention is designed for operation over an extensive temperature range. Condensation of water droplets or ice from the breath sample on reflecting surfaces may be prevented by heating these surfaces. This may be accomplished by applying electric current through the reflecting surface which may also perform as a resistive thin film. Operation at very high temperatures may be limited by thermal noise of the detector elements. Including small Peltier elements for thermoelectric cooling may extend the operation in this respect.

Preferably, the system includes one enclosure, housing all elements, thereby forming a confined, and physically integral unit. The support structure could be an integral part of the enclosure. The support structure should preferably be adapted for leak-proof connection of a mouthpiece.

The system exhibits minimum cross sensitivity between the determinations of the substances. This is achieved by optimisation of the system design, incorporating such elements as adaption of the radiation path lengths to the expected range of concentrations. The angular distribution of the radiation is also of high significance, since it will have influence on the dispersive properties. Other important factors are the spectral width of the dispersive element, and its suppression of radiation outside the transmission window.

Advantageously, the system is capable of determining whether a certain substance originates from the upper or lower respiratory tract. In a normal adult human subject, the upper airways have a volume of approximately 150 ml, corresponding to approximately 30% of the tidal volume, i e the total expired volume. In forced and prolonged expiration, the upper airway contribution will be approximately unchanged on an absolute scale. The expired air originating from the lower tract have both elevated $CO_2$ and humidity concentrations, whereas the air coming from the upper airways is normally humidified but with no $CO_2$ elevation.

Advantageously, a capability of over determination is provided, allowing the system to be self testing with respect to common error mechanisms, or by deliberate manipulation.

Advantageously, the support structure is being assembled from a small number of parts fabricated by injection polymer moulding.

One aspect of the present invention provides a system for the detection of at least one volatile substance in breath samples, the system comprising: one or more surfaces defining a flow path along which exhaled breath from a subject may flow; a radiation source, the one or more surfaces being substantially reflective to at least some of the radiation emitted by the radiation source, the radiation source being configured such that at least some radiation emitted thereby travels along the flow path and undergoes multiple reflections from the at least one surfaces; and at least one detector positioned to receive radiation emitted by the radiation source after multiple reflections thereof by the surfaces, and to perform analysis relating to portions of the radiation that have been absorbed since emission by the radiation source.

Advantageously, the flow path has a sufficiently large cross-section to allow substantially laminar flow of exhaled breath therethrough, such that regions of stagnant flow within said flow path comprise less than 10% of the transmission path of the radiation that travels along the flow path.

Preferably, the system comprises: a first detector adapted to receive radiation emitted by the radiation source after travelling a first distance along the flow path, and to perform analysis relating to portions of the radiation that have been absorbed since emission by the radiation source by $CO_2$ or water vapour; and a second detector adapted to receive radiation emitted by the radiation source after travelling a second distance along the flow path, and to perform analysis relating to portions of the radiation that have been absorbed since emission by the radiation source by at least one volatile substance.

Conveniently, the second distance is greater than the first distance.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

The detailed description of one embodiment of the system according to the invention will refer to the following drawings:

FIG. 3 is a diagram showing typical signals occurring during a procedure of breath sampling and analysis.

DETAILED DESCRIPTION OF THE INVENTION

Figure 1:
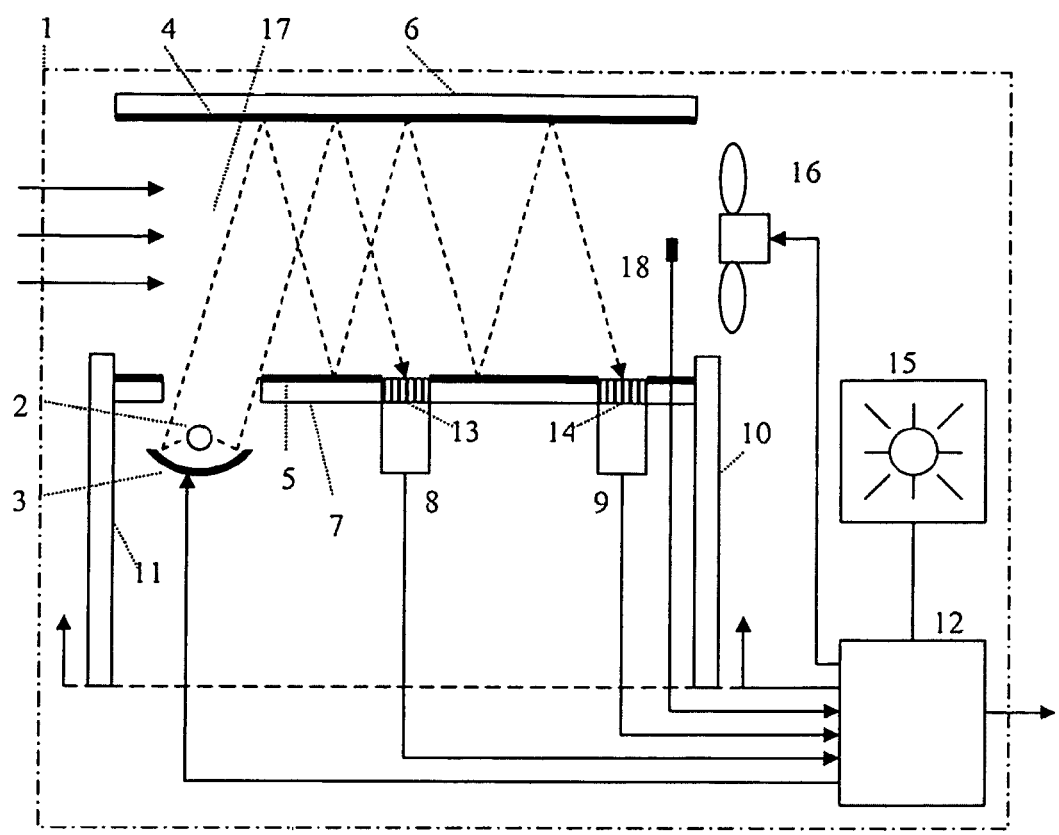
FIG. 1 is a schematic block diagram of the system according to one preferred embodiment.

One preferred embodiment of the system according to the invention is schematically depicted in FIG. 1. All system elements are being confined in a physical enclosure 1, the size of which is relatively modest, typically less than 100×50×40 mm, due to the miniaturization and small size of most of the included elements. The enclosure could be adapted and designed for mobile use, e g as a handheld unit, or stationary installation, e g in a vehicle.

A mechanical support structure 6, 7 defines a measuring cell 17 is provided with surfaces 4, 5 of high infrared reflectance, e g by being plated with a thin gold film, exhibiting a reflection coefficient for infrared radiation of 0.95 or higher. The support structure 6, 7 is used for precision positioning of a radiation source 2, a concave reflector 3, dispersive elements, e g interference filters, 13, 14, detectors 8, 9, e g thermopile or pyroelectric elements.

The optical arrangement of the measuring cell 17, including the support structure 6, 7 allows multiple reflections between the surfaces 4, 5 as indicated by the depicted zig-zag dotted line. The concave mirror 3 provides a collimated radiation beam stemming from the source 2. A first detector 8 including a first interference filter 13 adapted for the detection of $CO_2$ or water vapour is positioned to receive radiation after a relatively short path of typically 10 cm. A second detector 9 including a second interference filter 14 adapted for the detection of ethyl alcohol is positioned to receive radiation after a relatively long path, typically 15-50 cm. The path lengths are adapted to the range of concentrations expected in typical breath samples, and to the absorption coefficients of the respective substances. Using ten or more reflections, it is possible to confine a radiation path within a support structure having a physical size an order of magnitude smaller. A preferred implementation is to use concave reflecting surfaces opposing each other, each surface coinciding at one point with the centre of radius of curvature to the opposing surface.

The enclosure 1 and the measuring cell 17 typically has a tubular shape, with inlet and outlet openings (left and right, respectively, in FIG. 1) having cross section areas large enough to maintain a laminar flow within the measuring cell 17. Recessions, such as that provided by the source 2 and the mirror 3, may act as stagnant flow regions, with adverse effect on flow transit time, and consequently on the system response and recovery time. They should be minimised, and should not occupy more than 10% of the radiation transmission path.

The breath sample is collected by allowing it to flow through the support structure 6, 7, as depicted by the arrows at the left of FIG. 1. A pump 16 may provide active augmentation of the air flow in order to minimise eventually delayed response attributable to air transport. In its operating condition, the support structure 6, 7 includes relatively large openings, both to the left and to the right of the region in which radiation exposure occurs. This is necessary in order to obtain minimum air flow resistance. On the other hand, it may also allow dust particles and other contaminants to enter the support structure. Such contamination would deteriorate the performance of the system. Therefore, the support structure 6, 7 is provided with lids 10, 11, which are used for opening and closure, thus preventing any contaminants to enter at all times except during sampling. The lids 10, 11 thus act as alternating means to transform the support structure between the active and passive conditions. Preferably the lids 10, 11 are operated partly or fully automatic, by electromechanical means.

An electronic signal processing unit 12 is also provided. The signals from thermopile or pyroelectric detectors 8, 9 are typically of the order of 10-100 μV, and the transmission loss due to absorption of substances may be a very small fraction of this signal. It is therefore necessary to minimise electronic noise and interference in order to obtain adequate signal resolution. A preferred technique is to modulate the radiation source, and to use a synchronous amplifier with a high amplification factor, typically 100 000, or more.

Modulation of infrared sources is basically limited by the thermal time constants of these sources. Lasers and diode sources can be modulated at high frequencies, but the availability of such sources is scarce in the wavelength range of 3-10 μm in which most absorption peaks of interest are located. Blackbody radiators may be modulated to 10 Hz, which is adequate in terms of system response time. The system response time should preferably be of the order of the reaction time of a typical subject to visual stimuli, i e a fraction of a second, since he/she will then perceive the response to be essentially instantaneous. Modulation in the 10 Hz range is also adequate from the point of view of 1/f noise, which is becoming predominant in many detectors and amplifiers at lower frequencies.

Signal processing further includes analog to digital conversion, and incorporation of the signals into a microprocessor environment, allowing sequential, arithmetic and logical operations of high complexity, based on a program stored in the permanent memory of the device. A sequence of operations will follow, in which the signals from the detectors 8, 9 are compared to reference data stored either in permanent or temporary memory cells. The electronic unit 12 may include several standard integrated circuits on a circuit board, or may be totally integrated on a silicon die, as an application-specific integrated circuit (ASIC).

An indicator or display 15 is also provided to communicate commands or measuring results to the user. One command could instruct the subject to perform a forced expiration in the direction of the support structure 6, 7, thus allowing for the actual breath sampling.

The system typically also includes a temperature sensor 18, measuring the prevailing temperature within the measuring cell. Preferably, it has small thermal mass in order to minimise response time, and may be of resistance type, or a thermoelement. It is connected to the electronic unit 12, which provides for adequate formatting of the signal. The sensor 18 may also include self-heating capability, enabling air flow velocity measurements to be performed, using the principle of hotwire anemometry. Measurement of air flow velocity may be used for compensation of undesired flow dependence of the source 2. Such compensation may involve a negative feedback loop, or an open solution, in which compensation is provided in the calculation algorithm.

The system is preferably designed for redundancy, i e the critical variables are determined by more than one single operation, thereby minimising the risk of error. For example, a major error source is related to the radiation source and its possible variability in terms of output intensity and spectral distribution. By using one or several extra detectors tuned to specific wavelengths, it is possible to detect such variability as soon as it occurs, and deliver a warning signal. In a corresponding fashion it is possible to safeguard against any other type of errors which may occur, either by accident, or by deliberate manipulation.

From FIG. 1, and the functional description above, it should be concluded that the system according to the invention is built up from a limited number of elements, using non-critical assembly techniques. The materials used are either non-expensive, or used in such small quantity that the material cost becomes small.

Figure 2:
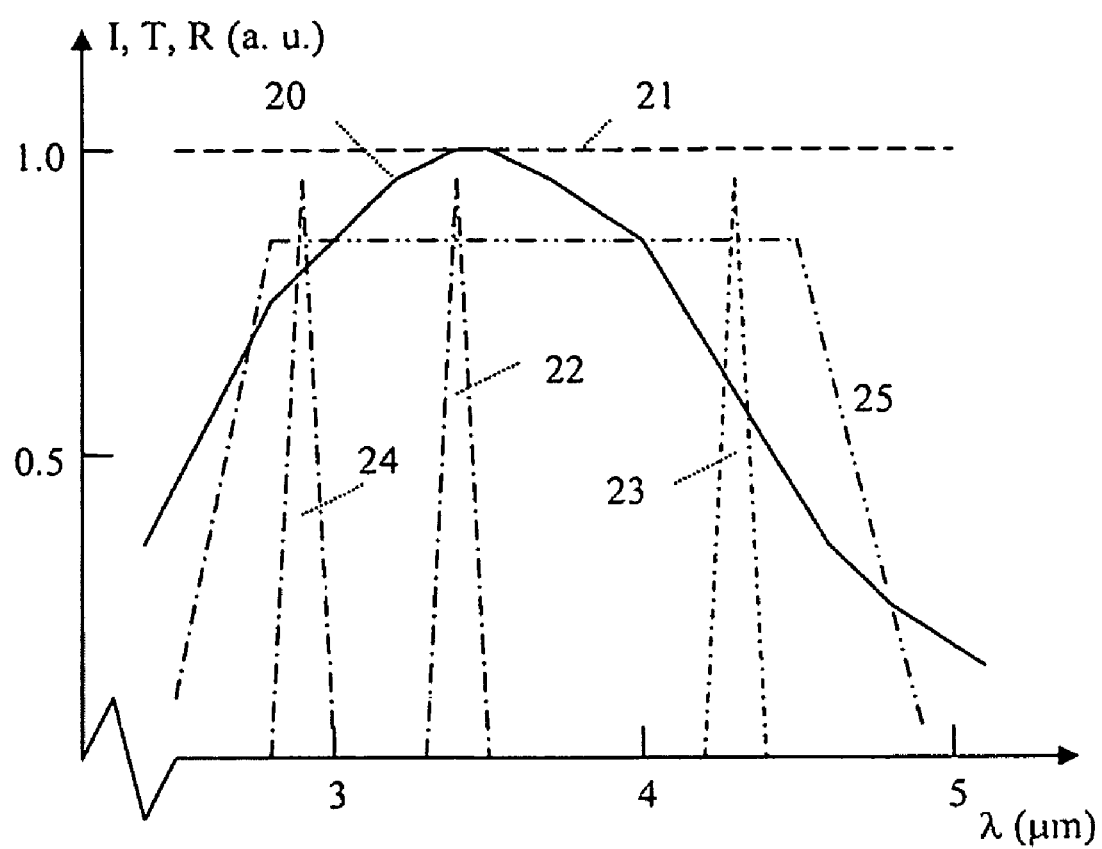
FIG. 2 is a diagram depicting typical and relevant infrared spectral properties of some of the constituting materials of the system.

FIG. 2 shows a diagram of typical performance of various components of the system with respect to infrared wavelength ranges. The curve 20 corresponds to the radiance of a typical blackbody source, operating at a temperature of approximately 600° C. A source of this kind thus operates as a broadband source over a relatively large range. Using several sources operating at different temperatures allows for further expansion of this range.

The curve 21 corresponds to the reflectance of polished gold as a function of wavelength, exhibiting a reflection coefficient of approximately 0.99. The corresponding value for aluminium is 0.98. It follows that a reflection coefficient of the order of 0.95 or higher is feasible with both materials. Five or even more reflections are thus realistic without significant loss of signal magnitude.

The curves 22, 23 and 24 correspond to the transmission of typical interference filters tuned to the absorption peaks of alcohol, $CO_2$ and water, respectively, at 3.4 and 4.26 and 2.8 µm. Typical widths of the transmission peaks are 50-200 nm. According to the present state of the art, interference filters may be designed very accurately, and with very high reproducibility. This is achieved by adapting the number of layers of an interference filter, and the tolerance of their thicknesses. The cross sensitivity between different substances is highly dependent on the actual design parameters of these filters. It may also be influence by adding materials, e g a substrate material for the interference filters, with sharp absorption edges as depicted in curve 25. A highpass filter with a sharp edge may consist of a semiconductor with a well-defined energy bandgap. The lowpass edge may be dependent on quantised molecular vibrations.

FIG. 3 shows schematically the variations in time of a number of entities associated with a breath sample of a subject, collected at close vicinity. The variables are: a) Flow velocity b) temperature c) relative humidity d) $CO_2$ concentration, and e) the expected output from a substance X present in the subject's blood.

Flow velocity (FIG. 3 a) will have a background level close to zero in the absence of active pump mechanism. At time=1 second, the subject is providing a forced expiration, approximately 1.5 seconds in duration. The air velocity promptly rises to more than one or several m/s, then declines. A relaxed expiration would be somewhat shorter in duration, and smaller in magnitude. Each single breath is easily distinguished at a measuring distance of 10-50 cm, since inspired air flow will not affect the recording. The magnitude of the signal declines with distance, and is also depending on the size of the 'orifice'.

Simultaneously with the onset of flow velocity, temperature will rise from the background level (room temperature 23° C. in FIG. 3b) to a level closer to body temperature. It will not reach body temperature, however, due to dilution of the sample. Furthermore, the downstroke of the temperature recording is expected to be less pronounced than the velocity recording, if there is no active mechanism for air transport.

In a similar manner, relative humidity (RH) will rise from ambient level (35% in FIG. 3c) to a level also depending on the dilution. The mucous membrane of the airways are normally effective humidifiers, resulting in almost 100% RH of undiluted expired air. The timing of the temperature and humidity recordings are expected to be nearly equal.

The $CO_2$ curve (FIG. 3) will start from a background level of almost zero, or 0.04-0.1%, depending on the ambient ventilation, 1000 ppm (0.1%) being accepted as the hygienic upper maximum. Alveolar air has a remarkably constant value of 5.3% in a normal resting subject, and exhibits modest variation with activity level, age, gender, etc. Measuring the absolute $CO_2$ concentration, i e the plateau value observed in FIG. 3 d), of the sample is thus a preferred method of determining the dilution. The onset of the $CO_2$ curve is somewhat delayed compared to the other curves, due to the effect of the upper airways representing a respiratory dead-space, approximately 150 ml, or 30% of the normal tidal volume (the volume of one relaxed breath) of a resting adult subject.

The signal representing a substance X is shown in FIG. 3 e). This recording has equal timing of the $CO_2$ recording, both having alveolar origin. In order for a breath sample to represent alveolar air, it is required that the $CO_2$ and sample waveforms exhibit a clear plateau. A superficial or uncompleted breath will not be representative of alveolar or blood concentrations.

From the description relating to FIG. 3, it should be clear that a number of prerequisites exist for the identification of a breath from a subject. These criteria can be used in order to make sure that the conditions for the determination are adequate. They may also be tools for avoiding manipulation.

From the description relating to FIG. 3 it is also evident that the dynamic properties of the detection and analysis process are central to the present invention. The requirement on the time resolution of the entire process is mainly determined by the speed of human perception, as earlier indicated. The requirement on the detection alone is mainly determined by the kinetics of respiration. As outlined in FIG. 3, a time resolution of fractions of a second is required.

It should be evident from both the general and detailed description of the present invention that the method and system may be useful for real-time monitoring, rather than for the analysis of single breath samples. The invention enables breath-by breath monitoring, and thereby the possibility of studying a number of physiological processes in more detail. It may e g be of interest to study the variations with time of certain substance concentrations, including that of alcohol.

As already outlined above, the method and system according to the invention may preferably be used in such a way that the processed output signals are determining a locking/unlocking condition for starting or driving a vehicle, or other machinery.

The system and method according to the invention are defined by the claims below, and are by no means limited to the embodiment described above.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

We claim:

1. A system for the detection and analysis of at least one volatile substance in breath samples of a subject comprising:
   at least one source of infrared radiation adapted to the wavelength range of specific absorption peaks of the substances;
   a plurality of reflecting surfaces configured for reflecting the radiation;
   at least one detector configured for receiving the radiation providing electrical output signals corresponding to the transmission of the radiation within wavelength intervals corresponding to the absorption peaks;
   at least one measuring cell including a mechanical support structure defining the position of the source, the reflecting surfaces and the detector, adapted for the reception and flow of the breath sample, and exposing the breath sample to the radiation;
   at least one electronic signal processing unit and an algorithm, the electronic signal processing unit configured to execute the algorithm and to analyze the signals with respect to pre-programmed information concerning infrared absorption spectra of the substances and to cooperate with the system for generating a response to the analyzed signals; and
   the response of the system being displayed or otherwise communicated, and perceived as essentially instantaneous, and wherein the system is configured to detect and analyze simultaneously a plurality of volatile substances including one of the volatile substances is carbon dioxide and to execute the algorithm which uses a first measured concentration of the carbon dioxide to determine the degree of dilution of the breath sample for adjusting a second measured concentration of another of the volatile substances to approximate the actual concentration of the another of the volatile substances in the breath sample.

2. A system according to claim 1 wherein the degree of dilution corresponds to the breath sample being diluted with ambient air.

3. A system according to claim 1 wherein the response of the system being mainly determined by the transit time of the breath sample through the measuring cell.

4. A system according to claim 1 wherein the response of the system being less than ten seconds.

5. A system according to claim 1 wherein the breath sample is collected in free air in the close vicinity of the subject.

6. A system according to claim 1 further comprising at least one replaceable mouthpiece adapted for leak-proof connection between the measuring cell and the mouth of the subject.

7. A system according to claim 1 wherein the measuring cell having an inlet and outlet openings of sufficient cross section area to maintain essentially laminar air flow within said measuring cell of the breath samples and regions of stagnant flow of the breath samples within the measuring cell occupying less than 10% of the transmission path of the radiation.

8. A system according to claim 1 wherein the measuring cell having a tubular structure.

9. A system according to claim 1 further comprising a means for the active transport of the breath sample through the measuring cell in the form of a pump or a fan.

10. A system according to claim 1 wherein the source is a heated filament constituting essentially a blackbody radiator, adapted for a modulation period shorter than the visual reaction time of normal subjects.

11. A system according to claim 1 wherein a path length of the radiation is larger than the physical dimensions of said measuring cell.

12. A system according to claim 1 wherein at least one of the reflecting surfaces being at least partly concave and having surface segments, the reflecting surface exhibiting a reflectance coefficient to the radiation exceeding 0.99, each of the surface segments of the concave reflecting surface coinciding at one point with a centre of radius of curvature of an opposing surface.

13. A system according to claim 1 wherein the radiation is at least partly collimated, and subjected to a plurality of reflections by the reflecting surfaces, the number exceeding five.

14. A system according to claim 1 further comprising at least one dispersive or absorptive element including at least one interference filter, or a high-resolution diffractive grating with fixed or electronically controllable properties.

15. A system according to claim 1 wherein the detector being a thermopile or a pyroelectric element.

16. A system according to claim 1 wherein the electronic signal processing unit includes at least one memory device for information storage, and providing the execution of pre-programmed sequence of logical and arithmetic operations.

17. A system according to claim 1 wherein the measurement of the concentration of carbon dioxide in the close vicinity of the subject being used, in combination with an estimated value of alveolar carbon dioxide concentration of the subject, to determine the degree of dilution of the breath sample.

18. A system according to claim 1 wherein the another of the volatile substances is ethyl alcohol or any other agent capable of affecting the subject's behaviour.

19. A system according to claim 1 further comprising a display means directed to the subject for communicating an instruction to provide the breath sample by forced expiration directed towards the measuring cell.

20. A system according to claim 1 wherein the support structure being transformable between one active operational condition in which openings to receive and dispose of the breath sample are provided, and one passive condition, in which the source, the reflecting surface, and the detector are protected from ambient exposure.

21. A system according to claim 20 further comprising electromechanical means for alternation between the conditions.

22. A system according to claim 21 wherein the alternation between the conditions is partly or fully automatic.

23. A system according to claim 1 further comprising a support structure configured for housing the source, the reflecting surfaces, and the detector thereby forming a confined, and physically integral unit, adapted as a handheld unit, or for stationary installation in a vehicle.

24. A system according to claim 1 wherein the system analyses the plurality of the volatile substances and the signals have minimum cross sensitivities between the determinations of the volatile substances.

25. A system according to claim 1 wherein the support structure is adapted for the attachment of at least one mouthpiece, by which an undiluted breath sample may be collected thereby resulting in the degree of dilution being nominal.

26. A system according to claim 1 wherein the response indicates whether the substances originate from the upper or lower respiratory tract.

27. A system according to claim 1 wherein the support structure being assembled from parts fabricated by injection moulding.

28. A system according to claim 1 further comprising at least one sensor for performing measurements of temperature or air flow velocity within the measuring cell.

29. A system according to claim 1 wherein the electronic signal processing unit provides a compensation of undesired interdependencies by means of a negative feedback loop or incorporation into a calculation algorithm.

30. A system according to claim 1 wherein the system provides the real-time monitoring of the output signals, including breath-by-breath analysis of substance concentrations.

31. A system according to claim 1 wherein the signals after processing determine a locking or unlocking condition for starting or driving a vehicle, or other machinery.

32. A method for the detection and analysis of at least one volatile substance in breath samples of a subject comprising the steps of:
 positioning a measuring cell within the expiratory air flow of a subject, allowing the reception and disposal of the breath sample;
 exposing the breath sample within the measuring cell to infrared radiation from at least one source within at least one wavelength range of specific absorption peaks of the substances;
 detecting the radiation after passage through the breath sample and thereby providing a plurality of output signals corresponding to the transmission of the radiation within wavelength intervals corresponding to the absorption peaks;
 the passage through the sample being elongated by a plurality of reflecting surfaces;
 analysing the signals with respect to pre-programmed information concerning infrared absorption coefficients of the substances including executing an algorithm with an electronic signal processing unit, wherein simultaneously a plurality of volatile substances are detected and analyzed including one of the volatile substances is carbon dioxide and the algorithm uses a first measured concentration of the carbon dioxide to determine the degree of dilution of the breath sample for adjusting a second measured concentration of another of the volatile substances to approximate the actual concentration of the another of the volatile substances in the breath sample; and
 displaying a response to the detection and analysis and enabling the response to be perceived as essentially instantaneous.

33. A method according to claim 32 wherein the response being determined by the transit time of the breath sample through the measuring cell.

34. A method according to claim 32 wherein the response to the detection being less than ten seconds.

35. A method according to claim 32 wherein the analysis including variations with time of said output signals.

36. A method according to claim 32 wherein the breath sample being collected and disposed of in free air in the close vicinity of the subject.

37. A method according to claim 32 further comprising assisting in the active transport of the breath sample through the measuring cell by means of a pump or fan.

38. A method according to claim 32 further comprising modulating the source, adapted for a modulation period shorter than the visual reaction time of a typical subject.

39. A method according to claim 32 wherein the dispersion or absorption of the radiation being performed by at least one interference filter, or high-resolution diffractive grating with fixed or electronically controllable properties.

40. A method according to claim 32 wherein the signal analysis being performed by at least one electronic signal processing unit including at least one memory device for temporary and permanent information storage, and at least one device for the execution of pre-programmed sequence of logical and arithmetic operations.

41. A method according to claim 32 wherein the measurement of the concentration of carbon dioxide in the close vicinity of the subject being used, in combination with an estimated value of alveolar carbon dioxide concentration, to determine the degree of dilution of the breath sample.

42. A method according to claim 32 wherein the another of the volatile substances in the breath sample is ethyl alcohol or any other agent related the subject's health or behaviour.

43. A method according to claim 32 wherein the displaying being directed to the subject for providing the breath sample by forced expiration directed towards the support structure.

44. A method according to claim 32 wherein the displaying indicates whether the substances originate from the upper or lower respiratory tract.

45. A method according to claim 32 wherein the determination of the substances involve redundant operations, providing capability of self-testing with respect to common accidental or deliberate errors.

46. A method according to claim 32 further comprising compensating of undesired interdependencies of the signals by means of a negative feedback loop or incorporation into a calculation algorithm.

47. A system according to claim 32 wherein the system providing the real-time monitoring of the output signals, including breath-by-breath analysis of substance concentrations.

48. A system according to claim 32 wherein the signals after processing are determining a locking or unlocking condition for starting or driving a vehicle, or other machinery.

* * * * *